United States Patent [19]
Koever et al.
[11] Patent Number: 4,957,872
[45] Date of Patent: * Sep. 18, 1990

[54] METHOD FOR THE DETERMINATION OF REDOX REACTIONS USING IODATE TO ELIMINATE ASORBIC ACID INTERFERENCE

[75] Inventors: Laszlo Koever; Walter Rittersdorf; Wolfgang Werner, all of Mannheim, Fed. Rep. of Germany

[73] Assignee: Boehringer Mannheim GmbH, Mannheim, Fed. Rep. of Germany

[ * ] Notice: The portion of the term of this patent subsequent to May 10, 2005 has been disclaimed.

[21] Appl. No.: 145,901

[22] Filed: Jan. 20, 1988

Related U.S. Application Data

[63] Continuation of Ser. No. 941,406, Dec. 15, 1986, Pat. No. 4,743,559, which is a continuation of Ser. No. 779,594, Sep. 24, 1985, abandoned, which is a continuation of Ser. No. 246,807, Mar. 23, 1981, abandoned.

[30] Foreign Application Priority Data

Mar. 29, 1980 [DE] Fed. Rep. of Germany ....... 3012368

[51] Int. Cl.[5] ........................ G01N 1/00; G01N 21/78
[52] U.S. Cl. ...................................... 436/175; 422/56; 435/28; 436/66; 436/95; 436/135; 436/825; 436/904

[58] Field of Search ........................ 435/28; 252/408.1; 422/56, 57; 436/66, 95, 135, 175, 825, 904

[56] References Cited

U.S. PATENT DOCUMENTS

| | | | |
|---|---|---|---|
| 3,411,887 | 11/1968 | Ku | 422/57 |
| 4,076,502 | 2/1978 | Dugle et al. | 435/28 |
| 4,168,205 | 9/1979 | Daninger et al. | 435/28 |
| 4,298,688 | 11/1981 | Kallies | 422/56 |
| 4,743,559 | 5/1988 | Koevér et al. | 436/135 X |

*Primary Examiner*—Robert J. Hill
*Attorney, Agent, or Firm*—Felfe & Lynch

[57] ABSTRACT

The present invention provides a process for the detection of redox reactions by introducing a redox reagent system into a test system, wherein a soluble iodate is additionally added to the test system in an amount which is in excess of the highest amount of disturbing reducing agents present in the test system.

The present invention also provides a diagnostic agent for the detection of redox reactions containing a redox reagent system, wherein the test system used additionally contains an iodate which is soluble therein in an amount which is in excess of the highest amount of disturbing reducing agents present in the test system.

15 Claims, No Drawings

METHOD FOR THE DETERMINATION OF REDOX REACTIONS USING IODATE TO ELIMINATE ASORBIC ACID INTERFERENCE

This application is a continuation of Ser. No. 941,406, filed Dec. 15, 1986 which is now U.S. Pat. No. 4,743,559, which is a continuation of Ser. No. 779,594, filed Sept. 24, 1985, now abandoned, which is a continuation of Ser. No. 246,807, filed Mar. 23, 1981, now abandoned.

This invention relates to a method and a diagnostic agent for the detection of redox reactions. More specifically, the present method and agent introduce a redox reagent system into a test system, by adding a soluble iodate in an amount in excess of the total of disturbing reducing agents present in the test system. Such disturbing reducing agents include especially ascorbic acid.

In clinical and pharmaceutical chemistry, in biochemistry and in foodstuff chemistry, redox systems are of great importance for determination methods for substrates and enzymes. There is a very large variety of photometric processes for such methods of determination. However, the so-called rapid diagnostics are of especial importance, these being agents which contain all the reagents in dry form in absorbent carriers or in films. The agents are brought into contact with the liquids to be investigated and the resulting colours can be assessed visually or with a reflection photometer.

The materials to be investigated in the above-mentioned fields of chemical analysis, for example urine, blood, foodstuffs, pharmaceutical compositions and the like, frequently contain more or less large amounts of reducing agents, the commonest of which is ascorbic acid. It is clear that redox reactions can be considerably disturbed by strong reducing agents, such as ascorbic acid. Thus, it is known that, in the case of the detection of glucose with rapid diagnostics based upon the reaction of GOD-POD-redox indicators, falsely negative results can be brought about by ascorbic acid The hydrogen peroxide resulting from glucose with the help of GOD (glucose oxidase), reacts with POD (peroxidase) on the ascorbic acid instead of on the indicator, with oxidation, and thus is removed from the determination.

Furthermore, it is known that rapid diagnostics for the detection of blood in urine also give falsely negative results in the presence of ascorbic acid, the ascorbic acid apparently reducing the colored material formed by oxidation catalyzed by haemoglobin.

As an example of the falsely positive findings due to ascorbic acid, mention may be made of the determination of NADH or NADPH with the help of the reduction of tetrazolium salts to give colored formazanes. Ascorbic acid here acts in the same manner and increases the measurement signal.

Because of the special importance and the extent of the disturbances due to reducing agents and especially to ascorbic acid, attempts have been made to remove them from the fluids to be investigated or to develop processes and agents which are not disturbed by them. Thus, for example, the following processes are known:

oxidation with iodine solution and removal of excess iodine with thiosulphate;

oxidation with manganese dioxide and filtering off of the unused oxidation agent;

oxidation with alkaline hydrogen peroxide;

treatment of the test solution with anion exchangers.

All these processes necessitate a laborious treatment of the sample solution. Furthermore, especially in the case of rapid diagnostic agents, an integrated solution to the problem is very laborious. Test papers are also known in which urine must first be chromatographed through a zone containing an anion exchanger (see Federal Republic of Germany Pat. Specification No. 15 98 008) in order then, upon running further, to be able to react without disturbance in the actual reagent zone. Tests with such ion exchanger zones are commercially available for glucose and galactose. However, they have a complicated construction and, due to the necessary chromatographing time, the analysis time is considerably increased in comparison with conventional rapid tests.

Another possibility for removing ascorbic acid from liquids or for overcoming the disturbance of diagnostic agents depends upon the addition of ascorbate oxidase in optical tests and rapid diagnostics (see Federal Republic of Germany Pat. Specification No. 26 25 834).

Although this process is especially useful in the case of small ascorbic acid concentrations, the problem as a whole cannot be regarded as having been solved for the following reasons:

ascorbate oxidase only reacts with ascorbic acid itself but not with metabolites thereof, such as the glucuronide and the sulphate, or with other reducing agents;

the oxidation of ascorbic acid by ascorbate oxidase is relatively slow so that in the case of test fluids which can contain more than 100 mg. ascorbic acid/dl., uneconomically large amounts of ascorbate oxidase must be used in order to ensure the overcoming of the disturbance to a reasonable extent;

in certain cases, the enzyme ascorbate oxidase is destroyed relatively quickly by aggressive reagents. Thus, for example, the cumol hydroperoxide used in a urine blood test must be enclosed in microcapsules (see U.S. Pat. Specification No. 4,129,417).

Surprisingly, we have now found that a process and a diagnostic agent, especially a rapid diagnostic, can be obtained which are not disturbed by ascorbic acid and its metabolites, even when these are present in relatively large amounts, when iodate is additionally added to known formulations or to the test system to be investigated.

Thus, according to one aspect of the present invention, there is provided a process for the detection of redox reactions by introducing a redox reagent system into a test system, wherein a soluble iodate is additionally added to the test system in an amount which is in excess of the highest amount of disturbing reducing agents present in the test system. It is surprising that iodate oxidizes the ascorbic acid sufficiently quickly but not the substrates important in clinical chemistry nor, furthermore, many of the redox indicators conventionally used in analysis and their corresponding colored reaction products, as well as conventional adjuvants. Thus, for example, under the usual analysis conditions (pH 5–9) and within the usual analysis times, the following are not attacked by iodate:

substrates: carbohydrates (glucose, galactose and the like), cholesterol, glycerol (from triglycerides), uric acid, NADH, NADPH, etc.

substrate glucose oxidase, galactose oxidase, oxidases: cholesterol oxidase, glycerol oxidase, uricase, etc.

indicators: benzidine derivatives (o-tolidine, 3,3',5,5'-tetramethylbenzidine), heterocyclic azines (azino-bisbenzothiazolonesulphonic acid), formazanes obtained as reduction products of tetrazolium salts, etc.

peroxidases: horse radish peroxidase, haemoglobin (blood)

adjuvants: aryl semicarbazides, which have been described as stabilizers for oxidation indicators (see Federal Republic of Germany Pat. Specification No.27 16 060).

That this property of iodates is surprising and could not be deduced, for example, from the oxidation potential is shown by a comparison with other halogen compounds, the standard potentials (under basic conditions) of which are, according to Cotton-Wilkinson, "Anorganische Chemie", pub. Weinheim, 1970, 2nd edn., page 532, as follows:

| | |
|---|---|
| iodate | +0.26 V |
| periodate | +0.39 V |
| iodine | +0.54 V |
| bromate | +0.61 V |
| chlorate | +0.63 V |

Whereas only periodate and free iodine, besides ascorbic acid, oxidize most indicators and especially the benzidine derivatives, bromate and chlorate, in spite of their higher oxidation potentials, are not able to oxidize ascorbic acid and thus are completely useless for the desired purpose. Furthermore, as far as iodates are concerned, it was previously assumed that they only oxidized ascorbic acid in acetic acid solution (see R. Indovina and D. Elia, Boll. Soc., Ital. Biol. sperm., 20, 390–393/1945; Chem. Abs., 40, 6110/1946).

According to a further aspect of the present invention, there is provided a diagnostic agent for the detection of redox reactions containing a redox reagent system, wherein the test system used additionally contains an iodate which is soluble therein in an amount which is in excess of the highest amount of disturbing reducing agents present in the test system.

The rapid diagnostic agents according to the present invention are practically not destroyed by ascorbic acid and are simple to produce by admixing an iodate with the formulations of known tests. Such known tests include, for example, the following: test papers for the detection of blood in urine with organic hydroperoxides and o-tolidine (see Federal Republic of Germany Pat. Specifications Nos.22 35 152; 26 40 211 and 12 42 905) and tetramethylbenzidine (see Federal Republic of Germany Pat. Specifications Nos. 24 60 903 and 27 16 060);

test papers for the detection of glucose in urine with GOD, POD and o-tolidine (see Federal Republic of Germany Pat. Specifications Nos. 24 15 257 and 11 21 847 and Austrian Pat. Specification No.19 88 96), 3,3',5,5'-tetramethylbenzidine (see Federal Republic of Germany Pat. Specification No. 24 60 903). substituted aminocarbazoles (see Federal Republic of Germany Pat. Specifications Nos. 22 05 733 and 23 38 932) and heterocyclic azines (see Federal Republic of Germany Pat. Specification No. 16 48 840);

test papers for the detection of galactose in urine with galactose oxidase, POD and o-tolidine (see U.S Pat. Specification No. 3,362,886);

test papers of diverse substrates with specific oxidases, POD and o-tolidine (see U.S. Pat. Specification No. 3,099,605);

test films for the determination of glucose in blood with GOD, POD, o-tolidine (see Federal Republic of Germany Pat. Specification No. 15 98 153) and 3,3',5,5'tetramethylbenzidine (see Federal Republic of Germany Pat. Specification No. 24 60 903); and test papers for the determination of NADH or NADH-forming substrates or enzymes with tetrazolium salts and diaphorase (see Federal Republic of Germany Pat. Specification No. 24 52 283).

Since most of the above-mentioned tests are carried out in aqueous solutions, water-soluble iodates are advantageously used. Practically all water-soluble salts of iodic acid with inorganic and organic cations can be used provided that they do not disturb the analytical process. These are, in particular, the alkali metal salts, which are easily obtainable and some of which are commercially available, as well as the alkaline earth metal salts, ammonium salts and the salts with simple amines, for example piperidine, piperazine and the like.

Only in special cases are certain modifications of the conventional formulations necessary:

In the case of the large-scale production of test papers, amongst other things, relatively long impregnation times are necessary. In the course of these long impregnation times, under certain circumstances, a partial oxidation of the indicator can occur in the impregnation solution This is, for example, the case with the substituted aminocarbazoles used according to Federal Republic of Germany Pat. Specification No. 22 05 733. In these cases, it is preferable to bring about a certain spatial separation of the reagents by first impregnating the test paper with all the other reagents and thereafter post-impregnating with an appropriate iodate from an organic solvent which does not dissolve out the other components of the formulation. Examples of organo-soluble iodates include quaternary ammonium iodates, as well as salts of iodic acid with comparatively long-chained amines.

In cases where, due to the use of iodate, stability problems occur in the tests, use can be made of generally known measures for improving stability, such as a successive impregnation from different solvents, possibly with the addition of appropriate separating agents, for example polymers.

The use of iodates in rapid diagnostics is only expedient within the following pH limits: At pH values below about 4.5, in the case of the reduction of iodate by ascorbic acid, free iodine is formed in increasing amounts which, as already stated, oxidizes many indicators. Furthermore, in acidic media, iodate possesses an oxidation potential of 1.20 V (Cotton-Wilkinson, v. supra) and is, therefore, no longer compatible with most indicators and other formulation components;

Above pH 7–8, the oxidation of ascorbic acid by iodate becomes increasingly slower so that, for an effective removal of disturbances, excessively large amounts of iodate are necessary, which can give rise to difficulties in working up and possibly to storage problems.

The iodates are preferably used in 2 to 20 fold molar excess, referred to the amount of ascorbic acid present in the fluids to be investigated. Since the oxidation of the ascorbic acid must have taken place practically before the actual detection reaction, for detection reactions which proceed quickly, a larger excess of iodate is necessary than for slower reactions. Since, as already mentioned above, the oxidation of ascorbic acid slows down at a high pH, in these cases, too, a larger excess of iodate must be used. In any case, the correct amount of iodate is easy to determine by a simple series of experiments.

In comparison with known disturbance-free or low disturbance rapid diagnostics, the rapid diagnostics according to the present invention have the following advantages:

the use thereof is precisely the same as that of the previously used rapid diagnostics, some of which have long been known:

the production thereof is simple and is substantially the same as the conventional methods of production; in comparison with rapid diagnostics which contain ascorbate oxidase, in some cases they bring about a higher degree of removal of disturbances and, in particular, they are much cheaper to produce.

The use of iodate is, in itself, not limited to an incorporation into rapid diagnostics. Thus, for example, iodate can be added directly to the solution to be investigated and the solution thereby freed from disturbing reaction agents can be further investigated in known manner photometrically or with conventional rapid tests. However, it is to be pointed out that, in such a solution, tests, the substrates or reagents of which react with iodate, can no longer be carried out. Thus, for example, in the case of investigating urine with multitests, there are tests for nitrite and bile coloring materials (urobilinogen and bilirubin). These materials are oxidized by iodates in the acidic media of the test paper even before the detection thereof. Furthermore, the aromatic amines employed for conventional nitrite tests are oxidized to give strongly colored compounds.

Whether or not a particular test is disturbed by the addition of iodate can easily be ascertained by comparing standards with and without the addition of iodate.

In certain cases, for example in the case of analysis processes which are carried out at pH 5 to 6, where ascorbic acid is oxidized very quickly by iodate, it can be advantageous to add the iodate to the reagent composition or to parts thereof and thus substantially to simplify the course of the analysis. Thus, for example, in the case of the analysis of serum, the iodate is added to the conventional, weakly acidic deproteinization agent, for example uranyl acetate, a substantially undisturbed test solution thereby being obtained.

The diagnostic agent according to the present invention preferably contains 0.5 to 2 g. of iodate per 100 ml. of test system and preferably also has a pH value such that, together with the test system, a pH value of 5 to 9 is obtained.

Preferably the pH value of the test system is increased via the addition of the redox reagent system. Most preferably, the pH increase is from 5–6 to one of from 7–9.

A large variety of redox reagent systems can be present in the diagnostic agent according to the present invention, one preferred redox reagent system comprising an oxidation indicator, a hydroperoxide, a peroxidase and conventional adjuvants and another preferred redox reagent system comprising a reduction indicator, a reducing agent and optionally an electron carrier.

The diagnostic agents are preferably rapid tests in which the reagent system is impregnated into an absorbent carrier which is insoluble in the test system or is incorporated into a film which swells in the test system, which film may be fixed on to a solid carrier, for example on to a synthetic resin film. The reaction is then, after moistening with the test system, determined on the basis of the coloration which appears.

However, the diagnostic agents can also be soluble in the test system and be present, for example, as a solution, lyophilisate or reagent tablet or can be incorporated into a test film which is soluble in the test system. The reagents are then mixed with the test system and possibly with further solvents and the reaction is determined photometrically in a cuvette.

By test systems, there are to be understood the samples to be investigated, possibly with the addition of appropriate solvents. By the reagent system, there is to be understood the totality of the reacting materials and all other adjuvants, such as buffer, wetting agent, viscosity-regulating materials, stabilizing agents and contrast coloring agents, as well as possibly solvents and the like.

The following Examples are given for the purpose of illustrating the present invention:

EXAMPLE 1

Test paper for the detection of blood (erythrocytes) in urine.

Filter paper (Schleicher & Schüll No. 23 is successively impregnated with the following solutions and, after each impregnation, dried at 40° C.:

| | |
|---|---|
| Solution 1. | |
| 1.2 molar citrate buffer, pH 5.25 | 35.0 ml. |
| ethylenediamine-tetraacetic acid, disodium salt | 0.1 g. |
| dioctyl sodium sulphosuccinate | 0.5 g. |
| 2,5-dimethylhexane-2,5-dihydroperoxide (about 70%) | 1.6 g. |
| phosphoric acid trimorpholide | 12.7 g. |
| sodium iodate | 0.5 g. |
| ethanol | 30.0 ml. |
| distilled water | ad 100.0 ml. |
| Solution 2. | |
| 3,3',5,5'-tetramethylbenzidine | 0.3 g. |
| phenanthridine | 0.2 g. |
| 1-phenylsemicarbazide | 0.02 g. |
| toluene/methanol (60:40 v/v) | ad 100.0 ml. |

The presence of 5 erythrocytes/$mm^3$ can still be determined with this test paper in the presence of 150 to 200 mg. ascorbic acid/dl. In the case of an analogous test paper which, instead of the iodate, contains $3\times10^4$ U ascorbate oxidase, the positive reaction is only visible up to a concentration of 30 to 50 mg. ascorbic acid/dl. and, in the case of a paper without additives, only up to a concentration of about 10 mg. ascorbic acid/dl. If the test paper according to the present invention is heated for 3 days to 60° C., then it still retains its sensitivity. The paper with ascorbate oxidase only reacts, after this stressing, like a paper without additives.

EXAMPLE 2

Test paper for the semiquantitative determination of glucose in urine.

Filter paper (Schleicher & Schüll No.597 NF-Ind.) is successively impregnated with solutions of the following compositions and, after each impregnation, dried at 50° C.:

| | |
|---|---|
| Solution 1. | |
| glucose oxidase (71 U/mg.) | 1.2 g. |
| peroxidase (66 U/mg.) | 0.2 g. |
| 1.2 M citrate buffer, pH 5 | 50.0 ml. |
| 9-(γ-dimethylaminopropyl)-6-chloro-3-aminocarbazole dihydrochloride | 2.1 g. |
| tartrazine | 0.12 g. |
| laurol sarcosine | 1.1 g. |
| distilled water | ad 100.0 ml. |

-continued

| Solution 2. | |
|---|---|
| tetramethylammonium iodate | 1.4 g. |
| ethanol | ad 100.0 ml. |

A test paper is prepared in a similar manner but is only impregnated with Solution 1. Urine samples were prepared containing 100, 300 and 1000 mg. glucose/dl., into each of which was introduced 0, 50, 100 and 200 mg. ascorbic acid/dl.

The test papers were dipped into the urine samples and then placed upon an absorbent substrate. One minute after dipping in, their reaction colors were compared, the urine without ascorbic acid thereby being taken as an inner standard. As can be seen from the following Table, in which the values given are expressed in mg. glucose/dl., the disturbance due to the ascorbic acid is removed by the addition of iodate:

| | amount of ascorbic acid/dl. | | | |
|---|---|---|---|---|
| iodate | 0 | 50 | 100 | 200 |
| − | 100 | negative | negative | negative |
| + | 100 | 100 | 100 | 100 |
| − | 300 | 100 | negative | negative |
| + | 300 | 300 | 300 | 300 |
| − | 1000 | 300 | 100 | negative |
| + | 1000 | 1000 | 1000 | 1000 |

EXAMPLE 3

Test paper for the detection of glucose in urine.

Filter paper (Schleicher & Schüll No. 597 NF) is impregnated with a solution of the following composition and dried at 50° C.:

| | |
|---|---|
| glucose oxidase (71 U/mg.) | 0.38 g. |
| peroxidase (66 U/mg.) | 0.02 g. |
| potassium iodate | 2.00 g. |
| tartrazine | 0.08 g. |
| o-tolidine | 0.42 g. |
| ethanol | 33.0 ml. |
| distilled water | ad 100.0 ml. |

Urine samples containing 50 mg. glucose/dl., into which has been introduced 0, 50, 100 and 200 mg. ascorbic acid/dl., give practically the same green reaction color with this test paper.

An analogous test paper but without iodate only gives a positive reaction in ascorbic acid-free urine.

EXAMPLE 4

Test film for the determination of small glucose contents in blood or serum.

| Components: | | |
|---|---|---|
| polyvinyl acetate propionate dispersion (Propiofan 70 D) | | 45.0 g. |
| 1,85% solution of sodium alginate in 0,5 m phosphate buffer, pH 5.5 | | 35.0 g. |
| sodium nonyl sulphate, dissolved in 5.0 ml. water | | 0.75 g. |
| glucose oxidase (71 U/mg.) | dissolved in 10 ml. water | 0.2 g. |
| peroxidase (66 U/mg.) | | 0.25 g. |
| 3,3',5,5'-tetramethylbenzidine, dissolved in 5 ml. acetone | | 0.68 g. |

-continued

| Components: | |
|---|---|
| sodium iodate | 1.0 g. |

The components are well mixed, coated in a layer thickness of 200 μ on to a synthetic film substrate and dried for 35 minutes at 60° C.

Another film was produced in the same manner but without iodate.

Sera containing 20 mg. glucose/dl. and 0, 2.5 and 5.0 mg. ascorbic acid/dl. were applied dropwise to the films which, after 1 minute, were wiped and, after a further 2 minutes, the coloration was measured with a commercially available remission photometer (Reflomat), with the use of a linear 0 to 100 scale. The following results were obtained:

| | serum with ascorbic acid | | |
|---|---|---|---|
| test film | 0 mg./dl. | 2.5 mg./dl. | 5.0 mg./dl. |
| without iodate | 47 | 43 | 35 |
| with iodate | 46 | 45 | 45 |

EXAMPLE 5

Test paper for the detection of NADH

Filter paper (Schleicher & Schüll No. 23 SL) is impregnated with a solution of the following composition and dried at 50° C.:

| | |
|---|---|
| iodonitrotriphenyltetrazolium chloride | 0.2 g. |
| sodium iodate | 0.5 g. |
| nonylphenol polyglycol ether | 0.2 g. |
| diaphorase (32 U/mg.) | 0.05 g. |
| 0.15M phosphate buffer, pH 7 | 40.0 ml. |
| distilled water | ad 100.0 ml. |

A test paper was produced in the same manner but without iodate.

Both papers reacted with aqueous solutions of NADH with the same red coloration. When ascorbic acid is added to the NADH solutions, the papers without iodate reacted more strongly.

EXAMPLE 6

Determination of glucose in serum

Solutions:

deproteinising solution 1: 0.16% uranyl acetate in 0.9% sodium chloride solution deproteinising solution 2: 0.16% uranyl acetate and 0.05% sodium iodate in 0.9% sodium chloride solution reagent solution:

POD 0.8 U/ml., GOD 10 U/ml., azino-bis-benzthiazolonesulphonic acid ammonium salt 1.0 mg./ml. in phosphate buffer, pH 7 (100 mMol/liter)

Sample 1 serum with 100 mg. glucose/dl.

Sample 2 serum with 100 mg. glucose/dl. and 20 mg. ascorbic acid/dl.

Standard: 9.1 mg. glucose/100 ml. water

Deproteinisation

Pipette (ml.) and centrifuge according to the following scheme:

| | | | | |
|---|---|---|---|---|
| deproteinisation solution 1 | 1.00 | 1.00 | – | – |
| deproteinisation solution 2 | – | – | 1.00 | 1.00 |
| sample 1 | 0.10 | – | 0.10 | – |
| sample 2 | – | 0.10 | – | 0.10 |
| gives supernatant No. | 1.1 | 1.2 | 2.1 | 2.2 |

Analysis:

Pipette (ml.) according to the following scheme, incubated for 30 minutes at 25° C. and measure the extinction at 436 nm (d=1 cm.).

| | blank | standard | supernatant 1.1 | 1.2 | 2.1 | 2.2 |
|---|---|---|---|---|---|---|
| distilled water | 0.1 | – | – | – | – | – |
| standard | – | 0.1 | – | – | – | – |
| supernatant | – | – | 0.1 | 0.1 | 0.1 | 0.1 |
| reagant solution | 5.0 | 5.0 | 5.0 | 5.0 | 5.0 | 5.0 |
| E | 0.115 | 0.425 | 0.424 | 0.366 | 0.426 | 0.423 |
| E–E (blank) | – | 0.310 | 0.309 | 0.251 | 0.311 | 0.308 |

Results:

Calculated from C=100×E (sample)/E(standard)

| supernatant | 1.1 | 1.2 | 2.1 | 2.2 |
|---|---|---|---|---|
| ascorbic acid in sample | – | + | – | + |
| iodate in deproteinisation solution | – | – | + | + |
| result (mg./dl.) | 99.7 | 89.0 | 100.3 | 99.4 |

The disturbance brought about by ascorbic acid in Sample 2 is thus completely removed by iodate.

EXAMPLE 7

Determination of L-glutamic acid.

Solutions

Reagent solution 1:

1.2 ml. Triton×100

30 U diaphorase 10 mg. NAD 60 mg. iodonitrotriphenyltetrazolium chloride in 100 ml. 0.1M potassium phosphate/triethanolamine buffer, pH 8.6

Reagent solution 2:

90,000 U glutamate dehydrogenase in 100 ml. water

Sample 1

100 mg. L-glutamic acid in 100 ml. water

Sample 2

100 mg. L-glutamic acid and 40 mg. ascorbic acid in 100 ml. water

Iodate solution:

200 mg. sodium iodate in 100 ml. water

Preparation of samples:

Pipette (ml.) according to the following scheme and leave to stand for 15 minutes at ambient temperature:

| | | | | |
|---|---|---|---|---|
| sample 1 | 1.0 | 1.0 | – | – |
| sample 2 | – | – | 1.0 | 1.0 |
| $NaIO_3$ solution | – | 1.0 | – | 1.0 |
| distilled water | 1.0 | – | 1.0 | – |
| gives mixture No. | 1.1 | 1.2 | 2.1 | 2.2 |

Analysis:

Pipette (ml.) according to the following scheme, after 2 minutes measure the initial extinction $E_1$ at 492 nm (d=1 cm.), start with reagent 2 and after 15 minutes measure the end extinction $E_2$:

| | blank | mixture 1.1 | 1.2 | 2.1 | 2.2 |
|---|---|---|---|---|---|
| reagant solution 1 | 1.0 | 1.0 | 1.0 | 1.0 | 1.0 |
| distilled water | 2.0 | 1.8 | 1.8 | 1.8 | 1.8 |
| mixture | – | 0.2 | 0.2 | 0.2 | 0.2 |
| $E_1$ | 0.058 | 0.058 | 0.053 | creeps | 0.041 |
| reagant solution 2 | 0.03 | 0.03 | 0.03 | 0.03 | 0.03 |
| $E_2$ | 0.062 | 0.490 | 0.499 | creeps | 0.503 |
| $E_2-E_1$ (ΔE) | 0.004 | 0.432 | 0.446 | – | 0.454 |
| ΔE–ΔE (blank) | – | 0.428 | 0.442 | – | 0.452 |

Results:

Calculated from C=224×(ΔE-ΔE(blank))

| mixture No. | 1.1 | 1.2 | 2.1 | 2.2 |
|---|---|---|---|---|
| ascorbic acid in sample | – | – | + | + |
| iodate treatment | – | + | – | + |
| result (mg./dl.) | 95.9 | 99.0 | not readable | 101.2 |

The creeps of the extinction caused by the ascorbic acid (slow reduction of the tetrazolium salt), which prevents an exact measurement, can be prevented by pre-incubation of the sample solution with iodate, without the excess iodate disturbing the analysis.

It will be understood that the specification and examples are illustrative but not limitative of the present invention and that other embodiments within the spirit and scope of the invention will suggest themselves to those skilled in the art.

What is claimed is:

1. A method for determining an analyte in a test system which contains said analyte and ascorbic acid as an interfering reducing agent utilizing a redox reagent system, said redox reagent system comprising a redox indicator which forms a visually or photometrically detectable or assessible color by means of a redox reaction, comprising:

(a) contacting said redox reagent system with an amount of soluble iodate in excess of the amount necessary to remove ascorbic acid in said test system;

(b) contacting said test system to said soluble iodate and redox reagent system;

(c) reacting said ascorbic acid with said iodate at a pH of from 5 to 9 to eliminate said ascorbic acid as an interfering reducing agent; and determining in the presence of iodate in excess of the amount necessary to react with said ascorbic acid visually or photometrically detectable or assessable color as an indication of said analyte.

2. The method of claim 1, comprising reacting said ascorbic acid with said iodate at a pH of from 5 to 6.

3. The method of claim 1, wherein said soluble iodate is present in two to twenty fold molar excess as compared to the amount of ascorbic acid present.

4. The method of claim 1, comprising increasing the pH value of said test system by addition thereto of said redox reagent system.

5. The method of claim 4, wherein said pH is increased from 5-6 to 7-9.

6. A method for determining an analyte in a test system which contains said analyte and ascorbic acid as an interfering reducing agent utilizing a redox reagent system, said redox reagent system comprising a redox indicator which forms a visually or photometrically detectable or assessible color by means of a redox reaction, comprising:

(a) contacting said test system with an amount of soluble iodate in excess of the amount necessary to remove ascorbic acid in said test system;

(b) contacting said test system and said soluble iodate to said redox reagent system;

(c) reacting said ascorbic acid with said iodate at a pH of from 5 t 9 to eliminate said ascorbic acid as an interfering reducing agent; and (d) determining in the presence of iodate in excess of the amount necessary to react with said ascorbic acid visually or photometrically detectable or assessable color as an indication of said analyte.

7. The method of claim 6, comprising reacting said ascorbic acid with said iodate at a pH of from 5 to 6.

8. The method of claim 6, wherein said soluble iodate is present in two to twenty fold molar excess as compared to the amount of ascorbic acid present.

9. The method of claim 6, comprising increasing the pH value of said test system by addition thereto of said redox reagent system.

10. The method of claim 9, wherein said pH is increased from 5-6 to 7-9.

11. A method for determining an analyte in a test system which contains said analyte and ascorbic acid as an interfering reducing agent utilizing a redox reagent system, said redox reagent system comprising a redox indicator which forms a visually or photometrically detectable or assessible color by means of a redox reaction, comprising:

(a) simultaneously contacting said test system, said redox reagent system and an amount of soluble iodate in excess of the amount necessary to remove ascorbic acid in said test system;

(b) reacting said ascorbic acid with said iodate at a pH of from 5 to 9 to eliminate said ascorbic acid as an interfering reducing agent; and (c) determining in the presence of iodate in excess of the amount necessary to react with said ascorbic acid visually or photometrically detectable or assessable color as an indication of said analyte.

12. The method of claim 11, comprising reacting said ascorbic acid with said iodate at a pH of from 5 to 6.

13. The method of claim 11, wherein said soluble iodate is present in two to twenty fold molar excess as compared to the amount of ascorbic acid present.

14. The method of claim 11, comprising increasing the pH value of said test system by addition thereto of said redox reagent system.

15. The method of claim 14, wherein said pH is increased from 5-6 to 7-9.

* * * * *